(12) United States Patent
Ferrari et al.

(10) Patent No.: US 8,008,514 B2
(45) Date of Patent: Aug. 30, 2011

(54) PROCESS FOR PREPARING 2-METHOXYCARBONYLMETHYL-6,6-DIMETHYL-2-TETRAHYDROPYRAN CARBOXYLIC ACID

(75) Inventors: Massimo Ferrari, Cenate Sotto (IT); Paolo Belotti, San Paolo D'Argon (IT)

(73) Assignees: Erregierre S.p.A., S. Paolo D'Aragon (IT); Stragen Pharma SA, Geneva (CH)

( * ) Notice: Subject to any disclaimer, the term of this patent is extended or adjusted under 35 U.S.C. 154(b) by 149 days.

(21) Appl. No.: 11/988,856

(22) PCT Filed: Jul. 14, 2006

(86) PCT No.: PCT/EP2006/064273
§ 371 (c)(1),
(2), (4) Date: Jan. 15, 2008

(87) PCT Pub. No.: WO2007/009953
PCT Pub. Date: Jan. 25, 2007

(65) Prior Publication Data
US 2009/0043093 A1    Feb. 12, 2009

(30) Foreign Application Priority Data
Jul. 15, 2005   (IT) .............................. MI2005A1352

(51) Int. Cl.
*C07D 309/08* (2006.01)
(52) U.S. Cl. ...................................... 549/425
(58) Field of Classification Search ................... 549/425
See application file for complete search history.

(56) References Cited

FOREIGN PATENT DOCUMENTS
JP         03-077862      4/1991
WO       WO 99/48894    9/1999

OTHER PUBLICATIONS
International Search Report.

*Primary Examiner* — Patricia Morris
(74) *Attorney, Agent, or Firm* — Collard & Roe, P.C.

(57) ABSTRACT

Process for preparing 2-methoxycarbonylmethyl-6,6-dimethyl-2-tetrahydropyran carboxylic acid (I) comprising:
a) Reaction of 5-bromo-2-methyl-2-pentene (III) with magnesium and then diethyloxalate to obtain ethyl-2-oxo-6-methyl-5-heptenoate (IV);
b) Reaction of ethyl-2-oxo-6-methyl-5-heptenoate (IV) with an alkali amide and methyl acetate to obtain ethyl-2-methoxycarbonylmethyl-2-hydroxy-6-methyl-5-heptenoate (V);
c) Reaction of ethyl-2-methoxycarbonylmethyl-2-hydroxy-6-methyl-5-heptenoate (V) with an alkali metal hydroxide to obtain the corresponding 2-carboxymethyl-2-hydroxy-6-methyl-5-heptenoic acid (VI);
d) Cyclisation of 2-carboxymethyl-2-hydroxy-6-methyl-5-heptenoic acid (VI) with formic acid to give 2-carboxymethyl-6,6-dimethyl-2-tetrahydropyrancarboxylic acid (VII);
e) Monoesterification of 2-carboxymethyl-6,6-dimethyl-2-tetrahydropyrancarboxylic acid (VII) to 2-methoxycarbonylmethyl-6,6-dimethyl-2-tetrahydropyran carboxylic acid (I),
characterised in that in stage (e) the 2-methoxycarbonylmethyl-6,6-dimethyl-2-tetrahydropyran carboxylic acid (I) is purified by means of the formation of the corresponding salt with cyclohexylamine (IA).

16 Claims, 1 Drawing Sheet

Figure 1:
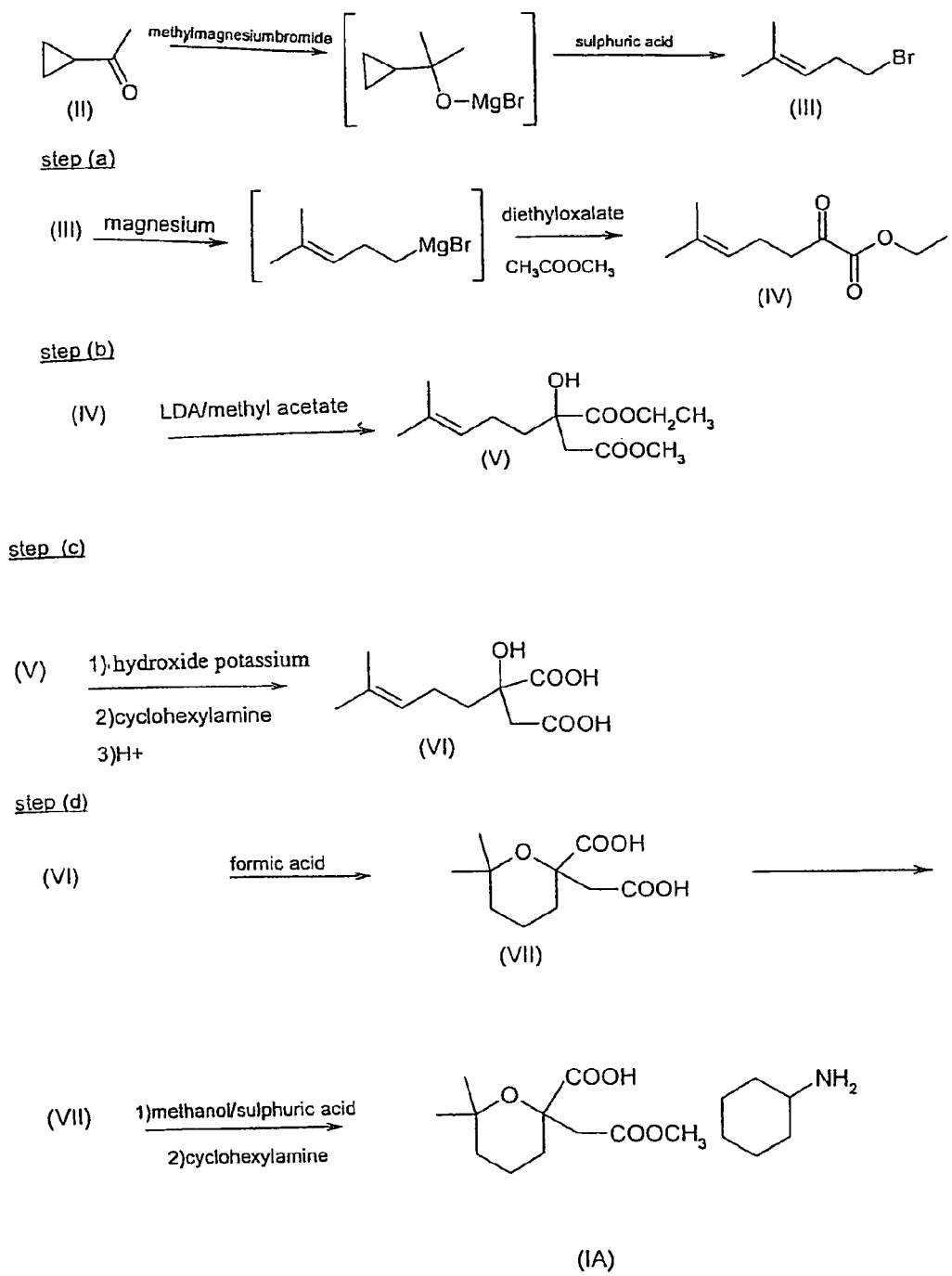

PROCESS FOR PREPARING 2-METHOXYCARBONYLMETHYL-6,6-DIMETHYL-2-TETRAHYDROPYRAN CARBOXYLIC ACID

CROSS REFERENCE TO RELATED APPLICATIONS

Applicants claim priority under 35 U.S.C.§119 of Italian Application No. MI 2005A001352 filed Jul. 15, 2005. Applicants also claim priority under 35 U.S.C.§365 of PCT/EP2006/064273 filed Jul. 14, 2006. The international application under PCT article 21(2) was published in English.

FIELD OF THE INVENTION

The present invention concerns a process for the preparation of 2-methoxycarbonylmethyl-6,6-dimethyl-2-tetrahydropyran carboxylic acid.

STATE OF THE ART 2-methoxycarbonylmethyl-6,6-dimethyl-2-tetrahydropyran carboxylic acid of formula (I)

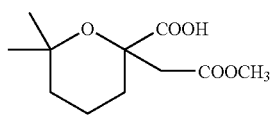

is a key intermediate in the synthesis of homoharringtonine, an alkaloid used as a chemotherapic agent.

In fact, as described in WO99/48894, the compound with formula (I) possibly converted into the corresponding anhydride is reacted in the presence of dicyclohexylcarbodiimide with cephalotaxine (IX)

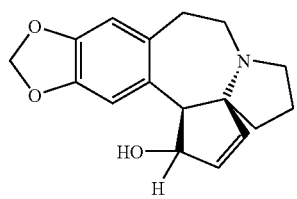

to obtain the homoharringtonine of formula (X)

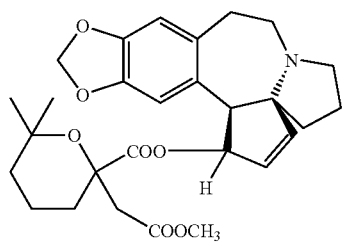

In the same prior art document a process is described for preparing the acid of formula (I) which contemplates the following stages:

a) reaction of 5-bromo-2-methyl-2-pentene (III)

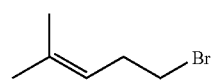

with magnesium and then diethyloxalate to obtain ethyl-2-oxo-6-methyl-5-heptenoate (IV)

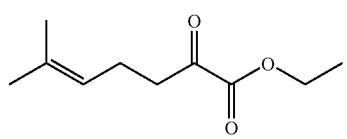

b) reaction of ethyl-2-oxo-6-methyl-5-heptenoate (IV) with an alkali amide and methyl acetate to obtain ethyl-2-methoxycarbonylmethyl-2-hydroxy-6-methyl-5-heptenoate (V)

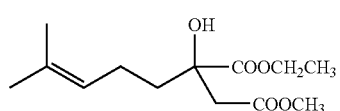

c) reaction of ethyl-2-methoxycarbonylmhyl-2-hydroxy-6-methyl-5-heptenoate (V) with an alkali metal hydroxide to obtain the corresponding 2-carboxymethyl-2-hydroxy-6-methyl-5-heptenoic acid (VI)

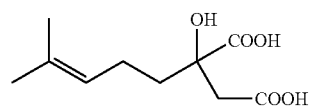

d) cyclisation of 2-carboxymethyl-2-hydroxy-6-methyl-5-heptenoic acid (VI) with formic acid to 2-carboxymethyl-6,6-dimethyl-2-tetrahydropyrancarboxylic acid (VII)

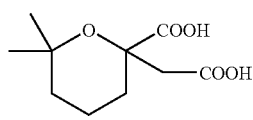

e) monoesterification of 2-carboxymethyl-6,6-dimethyl-2-tetrahydropyrancarboxylic acid (VII) to 2-methoxycarbonylmethyl-6,6-dimethyl-2-tetrahydropyran carboxylic acid (I), This process presents a series of drawbacks Firstly, the fact that the product of formula (I) is obtained in the presence of considerable quantities of by-products consisting of the product of formula (I')

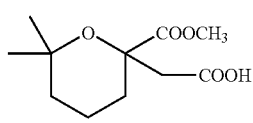

(I')

and of the diester of formula (I")

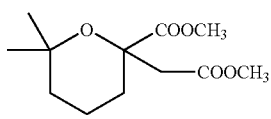

(I")

as well as of considerable quantities of non reacted acid (VII).

So to have an intermediate of formula (I) with high purity, purification must be carried out by column extraction, which may be performed either at the end of the above-mentioned stage (e) or in the subsequent homoharringtonine reaction. Column chromatography separation is not an industrial purification system. In addition, the process described in the above-mentioned prior art document contemplates further purifications such bulb to bulb distillation of the intermediate (IV) at the end of stage (a), and purification by column chromatography of the intermediate (V) at the end of stage (b), to obtain the pure intermediate (V), further decreasing the reaction yields of the end product, and thus making it even less likely that the process might be realised on an industrial scale.

The need was therefore felt to have a process for preparing the intermediate (I) which would not present the above disadvantages.

SUMMARY OF THE INVENTION

The Applicant has now surprisingly found a preparation process that overcomes the drawbacks of the above-mentioned process for preparing the intermediate of formula (I) which can be realised in an industrial scale.

The subject of the present invention is therefore the following process which comprises the following stages.

a) reacting 5-bromo-2-methyl-2-pentene (III) with magnesium and then diethyloxalate to obtain ethyl-2-oxo-6-methyl-5-heptenoate (IV);
b) reacting ethyl-2-oxo-6-methyl-5-heptenoate (IV) with an alkali amide and methyl acetate to obtain ethyl-2-methoxycarbonylmethyl-2-hydroxy-6-methyl-5-heptenoate (V);
c) reacting ethyl-2-methoxycarbonylmethyl-2-hydroxy-6-methyl-5-heptenoate (V) with an alkali metal hydroxide to obtain the corresponding 2-carboxymethyl-2-hydroxy-6-methyl-5-heptenoic acid (VI);
d) cyclising 2-carboxymethyl-2-hydroxy-6-methyl-5-heptenoic acid (VI) with formic acid to 2-carboxymethyl-6,6-dimethyl-2-tetrahydropyrancarboxylic acid (VII);
e) monoesterifying 2-carboxymethyl-6,6-dimethyl-2-tetrahydropyrancarboxylic acid (VII) to 2-methoxycarbonylmethyl-6,6-dimethyl-2-tetrahydropyran carboxylic acid (I), characterised in that in stage (e) 2-methoxycarbonylmethyl-6,6-dimethyl-2-tetrahydropyran carboxylic acid (I) is purified by the formation of the corresponding salt with cyclohexylamine (IA)

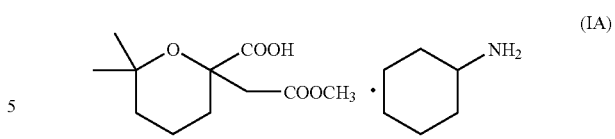

In fact the Applicant has surprisingly found that the above purification allows salified acid of formula (I) to be obtained with an HPLC purity higher than 92%, preferably higher than 95%. A further subject of the present invention is the above-mentioned salt of formula (IA).

In fact this salt, possibly transformed into the corresponding acid of formula (I) or into the respective anhydride, is used in the preparation of homoharringtonine as described above.

DESCRIPTION OF FIG. 1

FIG. (I) shows a synthetic diagram of a preferred embodiment of the process according to the present invention.

DETAILED DESCRIPTION OF THE INVENTION

Preferably in the process for preparing the compound of formula (I) the intermediates of formula (III), (IV), (V) and (VII) are not purified, while only one purification of the intermediate (V) is carried out at the end of stage (c) by converting this product into the corresponding cyclohexylamine salt (VIA)

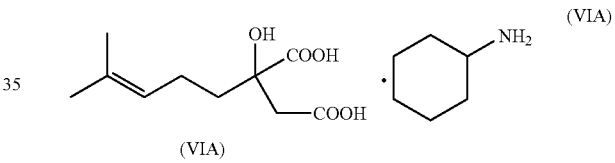

which before stage (d) is then transformed into the corresponding acid for treatment with strong mineral acid, even more preferably hydrochloric or phosphoric acid.

The salification of the acid (VI) to cyclohexylamine salt (VIA) is preferably carried out in a polar protic solvent, preferably in sec-butyl alcohol.

Stages (a)-(b) of the process according to the present invention are preferably carried out in a polar aprotic solvent, preferably tetrahydrofuran.

Preferably as an alkali amide in stage (b) of the process according to the present invention lithium diisopropylamide is used instead of the lithium bis(trimethyl)silylamide used in WO99/48894.

In fact the Applicant has found that by using lithium diisopropylamide it is possible to obtain the product of formula (IV) without having to purify the reagent (III).

The alkali hydroxide used in stage (c) of the process according to the present invention is preferably an aqueous solution of potassium hydroxide.

The monoesterification in stage (e) of the process according to the present invention is preferably carried out using methanol in the presence of a strong mineral acid, preferably concentrated sulphuric acid.

The salification of the product of formula (I) to the corresponding salt (IA) is carried out in a polar aprotic solvent, preferably methyl acetate.

5-bromo-2-methyl-2-pentene (III) used in stage (a) of the process according to the present invention is prepared by reacting cyclopropylmethylketone (II) react with methylmagnesium bromide and then with a strong mineral acid, preferably sulphuric acid in a polar aprotic solvent, preferably tetrahydrofuran.

Purely for illustrative purposes, without limitation, an example is given of the preparation of the compound of formula (I) in the form of the corresponding cyclohexylamine salt (IA) using the process according to the present invention.

EXAMPLE 1

Process for Preparing methoxycarbonylmethyl-6,6-dimethyl-2-tetrahydropyran Carboxylic Acid 105 kg of 12% methyl magnesium bromide in THF corresponding to 12.6 kg of the same with 100% concentration are charged into a stainless reactor.

Keeping the reaction temperature between 30 and 35° C. by cooling with a brine bath 6.7 kg of cyclopropylmethylketone (II) are poured. Once pouring is complete, the reaction mixture is stirred at 30-35° C. for at least 1 hour, then cooled to 5-10° C. and the reaction mixture is poured into another enameled reactor containing 60 kg of 35% sulphuric acid, cooled to 0-10° C.

The reaction mixture is brought to a temperature between 25 and 30° C. and kept at that temperature for at least 15 minutes, then the phases are left to superate, the lower aqueous phase is removed.

The organic phase is washed with 6.7 kg of demineralised water. It is stirred at 25-30° C. and left to decant to allow the separation of the two phases. The lower aqueous phase is removed.

The solvent is removed from the organic phase by vacuum distillation until an oily residue is obtained, to which 10.1 kg of THF are added and the mixture is stirred until it is completely dissolved. Then the solution is poured into a container with suitable capacity and sent to the next stage.

10 kg of product at 100% are obtained.

Yield: 77% referring to the kg of cyclopropylmethylketone (II).

1-2) Preparation of ethyl 2-oxo-6-methyl-5-heptenoate (IV)

1.55 kg of magnesium and 10 kg of THF are charged into a stainless steel reactor provided with liquid nitrogen cooling. This is heated under reflux (60-70° C.) and, still at that temperature, 0.5 l of the solution containing 10 kg of 5-bromo-2-methyl-pentene (II) at 100% is poured. This is kept under reflux for at least 10 minutes until the reaction starts. The reaction mixture is then cooled to 50-60° C. and, keeping it at that temperature with a brine bath, the remaining solution of 5-bromo-2-methyl-pentene (II) in THF is poured. The reaction mixture is kept at 50-60° C. for at least 1.5 hours and 40 kg of THF are added. The reaction mixture is then cooled with liquid nitrogen to −65/−70° C. and at that temperature 7.2 kg of diethyloxalate are added. The reaction mixture is kept at −65/−70° C. for at least 1 hour, under stirring. The mixture thus obtained is then poured into another enameled reactor containing 10 kg of 32% hydrochloric acid dissolved in 30 kg of demineralised water and previously cooled to 0-10° C.

The reaction mixture is then brought to 20-30° C. and left until the phases separate. The aqueous phase is removed, while the organic phase is washed at 20-30° C. with 0.25 kg of sodium bicarbonate dissolved in 5 kg of demineralised water. The reaction mixture is stirred at the same temperature and left until the phases separate. The lower aqueous phase is removed, while the solvent is removed from the organic phase by vacuum distillation until an oily residue is obtained. Then 15 kg of THF are added and the mixture obtained is stirred until a solution is obtained which is sent to the next stage.

Yield not determined.

1-3) preparation of ethyl-2-methoxycarbonylmethyl-2-hydroxy-6-methyl-5-heptenoate (V).

21.5 kg of a solution of 26% lithium diisopropylamide in THF are charged into a stainless steel reactor fitted with a liquid nitrogen cooling.

The reaction mixture is cooled to −70/−80° C. with liquid nitrogen and at that temperature 4.50 kg of methyl acetate are poured. The reaction mixture is then stirred at that temperature for at least 30 minutes. Then, still at that temperature, the whole solution of 5-ethyl-2-oxo-6-methyl-5-heptenoate obtained in the previous stage is poured. The reaction mixture obtained is kept always at −70/−80° C. for at least 30 minutes and is then poured into another enameled reactor containing 15.0 kg of 32% hydrochloric acid dissolved in 30 kg of demineralised water and previously cooled to 0-10° C. The reaction mixture is then brought to 20-25° C. and left until the phases separate. The aqueous phase is then eliminated. The solvent is removed from the organic phase by vacuum distillation until an oily residue is obtained Then 6.5 kg of methanol are added to the oily residue and this is stirred until a solution is obtained which is sent to the next stage.

1-4) Preparation of 2-carboxymethyl-2-hydroxy-6-methyl-5-heptenoic Acid (VI)

40 kg of demineralised water and 10 kg of potassium hydroxide are charged into a stainless steel reactor. This is stirred at 20-30° C. for 5 minutes, then at that temperature the whole solution of Ethyl-2-methoxycarbonylmethyl-2-hydroxy-6-methyl-5-heptenoate obtained in the previous stage is poured. The mixture is then heated under reflux (75-85° C.) and kept under stirring at the same temperature for at least 30 minutes. It is cooled to 25-30° C. and 13 kg of methylene chloride are added. It is stirred and then left until the phases separate. The lower organic phase is removed, while the aqueous phase is transferred into an enameled reactor, into which 20 kg of THF are then added.

The reaction mixture is kept at 25-30° C., while cooling it, and 19 kg of 32% hydrochloric acid are poured. The mixture is then stirred and left until the phases separate. The aqueous phase is removed, while 30.0 kg of sec-butyl alcohol are added to the organic phase. Starting from an initial temperature of 40-45° C., the temperature is allowed to rise to 55-60° C. and 6.0 kg of cyclohexylamine are poured.

The salt precipitates and the reaction mixture is cooled to 30-35° C. and centrifuged. The centrifuged product is washed with 15.0 kg of sec-butyl alcohol. All the solid obtained is then charged into a stainless steel reactor and 30 kg of demineralised water and 10 kg of methylene chloride are added; keeping the reaction mixture at 20-25° C., 9 kg of a solution of 30% sodium hydroxide are poured. Keeping it at the same temperature, 7.5 kg of 32% hydrochloric acid and 16 kg of ethyl acetate are added to the organic phase. The reaction mixture is then stirred at 20-25° C. and left until the phases separate. The aqueous phase is eliminated. The solution is weighed and analysed by potentiometric titration to determine its content of 2-carboxymethyl-2-hydroxy-6-methyl-5-heptenoic acid. 5 kg of the desired product at 100% are obtained. Yield with reference to the 10 kg of 5 bromo-2-methyl-pentene obtained in example 1-2): 37.7%.

1-5) Preparation of 2-methoxycarbonylmethyl-6,6-dimethyl-2-tetrahydropyran Carboxylic Acid (VII)

The solution obtained from the previous stage and containing 5 kg of 2-carboxymethyl-2-hydroxy-6-methyl-5-heptenoic acid 100% is charged into an enameled reactor. This residue is then cooled to 20-30° C. and 15 kg of formic acid 99% are added. The mixture is then heated to 70-75° C. and kept under stirring at that temperature for at least 4 hours. It is then cooled to 50-60° C. and the water is removed by vacuum distillation until an oily residue is obtained. The oily residue is cooled to 30-35° C. and 15 kg of ethyl acetate and 5 kg of demineralised water are added. The mixture obtained is stirred always at 30-35° C. and left under rest until the phases separate, eliminating the aqueous phase, while the solvent is removed from the organic phase by vacuum distillation until an oily residue is obtained. This residue is then cooled and 10.0 kg of methanol are added.

The mixture is then stirred until a solution is obtained and the solution obtained is sent to the next stage.

Yield not determined.

1-6) Preparation of 2-methoxycarbonylmethyl-6,6-dimethyl-2-tetrahydropyran Carboxylic Acid Salt of Cyclohexylamine (IA)

The whole solution obtained from the previous stage is charged into an enameled reactor. Keeping the temperature at 20-30° C. by cooling, 1.50 kg of 96% sulphuric acid are poured. The mass is kept at 25-30° C. for at least 6 hours. It is then cooled to 0-10° C. while pouring a solution of 5.5 kg of potassium bicarbonate in 16.5 kg of demineralised water. About 10.0 kg of solvent are distilled, which is removed and 5.0 kg of methylene chloride are added to the mixture obtained. The mixture obtained is then stirred at 30-35° C. and left under rest until the phases separate. The lower organic phase is eliminated, while 15 kg of methylene chloride are added to the aqueous phase, always keeping the mixture at 30-35° C. Then 4.00 kg of 85% phosphoric acid are poured and the mixture is left under rest until the phases separate. The aqueous phase is removed, while the solvent is removed from the organic phase by distillation until an oily residue is obtained to which 20.0 kg of methyl acetate are added. 3 kg of cyclohexylamine are added to the solution obtained. In this way the cyclohexylamine salt (IA) precipitates and the mixture containing the precipitate is kept at 25-30° C. for 30 minutes. It is then centrifuged and the centrifuged product is washed with 5 kg of methyl acetate. The product obtained is dried at 30-40° C. 3.5 kg of the desired product are thus obtained. Yield with reference to the 5 kg of 2-carboxymethyl-2-hydroxy-6-methyl-5-heptenoic acid (VI) obtained in example 1-4: 46.0%. HPLC purity >95%

The invention claimed is:
1. Process for preparing 2-methoxycarbonylmethyl-6,6-dimethyl-2-tetrahydropyran carboxylic acid (I) comprising the following stages:
a) Reacting 5-bromo-2-methyl-2-pentene (III) with magnesium and then diethyloxalate to obtain ethyl-2-oxo-6-methyl-5-heptenoate (IV);
b) Reacting ethyl-2-oxo-6-methyl-5-heptenoate (IV) with an alkali amide and methyl acetate to obtain ethyl-2-methoxycarbonylmethyl-2-hydroxy-6-methyl-5-heptenoate (V);
c) Reacting ethyl-2-methoxycarbonylmethyl-2-hydroxy-6-methyl-5-heptenoate (V) with an alkali metal hydroxide to obtain the corresponding 2-carboxymethyl-2-hydroxy-6-methyl-5-heptenoic acid (VI);
d) Cyclizing 2-carboxymethyl-2-hydroxy-6-methyl-5-heptenoic acid (VI) with formic acid to give 2-carboxymethyl-6,6-dimethyl-2-tetrahydropyrancarboxylic acid (VII);
e) Monoesterifying 2-carboxymethyl-6,6-dimethyl-2-tetrahydropyrancarboxylic acid (VII) to 2-methoxycarbonylmethyl-6,6-dimethyl-2-tetrahydropyran carboxylic acid (I),
wherein in stage (e) the 2-methoxycarbonylmethyl-6,6-dimethyl-2-tetrahydropyran carboxylic acid (I) is purified by means of the formation of the corresponding salt with cyclohexylamine (IA)

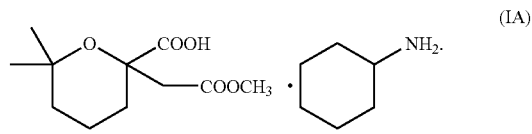

2. Process according to claim 1, wherein the intermediates (III), (IV), (V) and (VII) are not purified while only one purification of the intermediate (VI) is carried out at the end of stage (c)

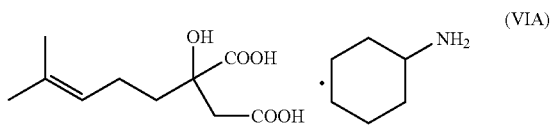

by the formation of the corresponding cyclohexylamine salt (VIA).

3. Process according to claim 2, wherein before stage (d) said salt (VIA) is transformed into the corresponding acid (VI) for treatment with a strong mineral acid.

4. Process according to claim 3, wherein said acid is chosen between hydrochloric acid and phosphoric acid.

5. Process according to claim 1, wherein the stages (a)-(c) are carried out in polar aprotic solvent.

6. Process according to claim 5, wherein said polar aprotic solvent is tetrahydrofuran.

7. Process according to claim 1, wherein in stage (b) lithium diisopropylamide is used as an alkali amide.

8. Process according to claim 1, wherein in stage (c) the alkali hydroxide is an aqueous solution of potassium hydroxide.

9. Process according to claim 1, wherein the monoesterification in stage (e) is carried out using methanol in the presence of a strong mineral acid.

10. Process according to claim 9, wherein said strong mineral acid is concentrated sulphuric acid.

11. Process according to claim 1, wherein the salification of the product of formula (I) to the corresponding salt (IA) is carried out in a polar aprotic solvent.

12. Process according to claim 11, wherein said polar aprotic solvent is methyl acetate.

13. Process according to claim 1, wherein the 5-bromo-2-methyl-2-pentene (III) used in stage (a) is prepared by reacting cyclopropylmethylketone (II) with methylmagnesium bromide and then with a strong mineral acid in a polar aprotic solvent.

14. Process according to claim 13, wherein said strong mineral acid is sulphuric acid and the polar aprotic solvent is tetrahydrofuran.
15. Process according to claim 13, wherein the 5-bromo-2-methyl-2-pentene (III) is used as a crude product in state in stage (a).
16. Salt of 2-methoxycarbonylmethyl-6,6-dimethyl-2-tetrahydropyran carboxylic acid with cyclohexylamine of formula (IA)
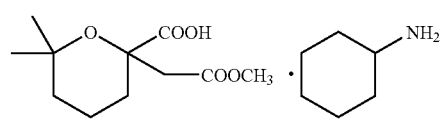
(IA)